United States Patent
Zombo

(10) Patent No.: US 8,986,778 B2
(45) Date of Patent: Mar. 24, 2015

(54) COATING METHOD FOR NON-DESTRUCTIVE EXAMINATION OF ARTICLES OF MANUFACTURE

(75) Inventor: Paul J. Zombo, Cocoa, FL (US)

(73) Assignee: Siemens Energy, Inc., Orlando, FL (US)

( * ) Notice: Subject to any disclaimer, the term of this patent is extended or adjusted under 35 U.S.C. 154(b) by 2240 days.

(21) Appl. No.: 11/481,721

(22) Filed: Jul. 6, 2006

(65) Prior Publication Data

US 2008/0008968 A1 Jan. 10, 2008

(51) Int. Cl.
- C08J 7/18 (2006.01)
- B05D 3/06 (2006.01)
- B05D 5/06 (2006.01)
- B32B 43/00 (2006.01)
- G01N 25/72 (2006.01)

(52) U.S. Cl.
CPC ...................... *G01N 25/72* (2013.01)
USPC ...... 427/10; 427/9; 427/8; 427/510; 427/552; 427/553; 427/557; 427/140; 427/142

(58) Field of Classification Search
None
See application file for complete search history.

(56) References Cited

U.S. PATENT DOCUMENTS

| | | | |
|---|---|---|---|
| 4,050,945 A | 9/1977 | Suzuki | |
| 4,080,959 A | 3/1978 | Leveen | |
| 4,179,926 A * | 12/1979 | Phillips et al. | 374/159 |
| 4,637,896 A * | 1/1987 | Shannon | 252/299.7 |
| 4,649,923 A | 3/1987 | Hoffman | |
| 4,931,420 A | 6/1990 | Asano et al. | |
| 5,111,048 A * | 5/1992 | Devitt et al. | 250/342 |
| 5,670,879 A * | 9/1997 | Zombo et al. | 324/227 |
| 5,934,805 A * | 8/1999 | Endo et al. | 374/5 |
| 6,200,088 B1 * | 3/2001 | Zombo et al. | 415/118 |
| 6,274,193 B1 * | 8/2001 | Rigney et al. | 427/142 |
| 6,399,948 B1 * | 6/2002 | Thomas et al. | 250/341.6 |
| 6,545,500 B1 * | 4/2003 | Field | 324/750.12 |
| 6,575,620 B1 * | 6/2003 | Banaszak et al. | 374/4 |

(Continued)

FOREIGN PATENT DOCUMENTS

| | | | | |
|---|---|---|---|---|
| JP | 57-114016 A | * | 7/1982 | 464/17 |
| JP | 2000-206100 A | * | 7/2000 | G01N 29/20 |
| WO | WO 03/102567 A1 | * | 12/2003 | G01N 27/20 |

OTHER PUBLICATIONS

Dibelrus et al., "non-destructive testing of corrosion affect on high-temperature protective coatings",VGB Kraftwerkstechnik 70, No. 9, 1990 (no month), pp. 645-651.*

(Continued)

*Primary Examiner* — Marianne L Padgett

(57) ABSTRACT

A method for non-destructive evaluation of an article of manufacture (30) by coating the article with a temperature-sensitive coating (34), stimulating the article with energy (18) to induce temperature changes in the article responsive to features of the article, then evaluating (24) a resulting topography of energy-induced changes (50, 52, 53) in the coating (34). The energy imparted to the article may be, for example, electromagnetic, magnetic, or sonic energy that produces localized changes in temperature in the article (30) in response to features (32) of the article such as flaws or other discontinuities. The coating (34) may be a suspension of liquid crystals in a liquid, and the energy may be an application of sonic energy. The coating may be a material that hardens (42, 54) or softens (44, 56) upon a slight increase in temperature. Layers (34, 35) of different energy-sensitive coatings (38, 40) may be applied to indicate different aspects of features of the article.

4 Claims, 4 Drawing Sheets

(56) References Cited

U.S. PATENT DOCUMENTS

| | | | |
|---|---|---|---|
| 6,602,594 B2 | 8/2003 | Miyata et al. | |
| 6,730,632 B2 | 5/2004 | Watanabe et al. | |
| 6,869,907 B2 | 3/2005 | Suzuki | |
| 6,932,876 B1* | 8/2005 | Statnikov | 148/558 |
| 7,376,518 B2* | 5/2008 | Subramanian et al. | 702/27 |
| 7,657,389 B2* | 2/2010 | Suh et al. | 702/104 |
| 8,050,883 B2* | 11/2011 | Sheiretov et al. | 702/127 |
| 8,173,964 B2* | 5/2012 | De Smet | 250/331 |
| 8,221,825 B2* | 7/2012 | Reitz et al. | 427/8 |
| 8,237,433 B2* | 8/2012 | Goldfine et al. | 324/238 |
| 8,742,347 B2* | 6/2014 | Altmann et al. | 250/332 |
| 2002/0049551 A1* | 4/2002 | Friedman et al. | 702/65 |
| 2002/0066770 A1* | 6/2002 | James et al. | 228/119 |
| 2002/0158626 A1* | 10/2002 | Shay et al. | 324/207.16 |
| 2004/0045162 A1* | 3/2004 | Beck et al. | 29/889.71 |
| 2004/0089812 A1* | 5/2004 | Favro et al. | 250/341.6 |
| 2005/0171703 A1* | 8/2005 | Goldfine et al. | 702/30 |
| 2005/0186327 A1* | 8/2005 | Saito et al. | 427/8 |
| 2005/0191447 A1 | 9/2005 | Kidnie et al. | |
| 2005/0255999 A1 | 11/2005 | Fisher | |
| 2005/0281989 A1 | 12/2005 | Finger | |
| 2006/0237104 A1* | 10/2006 | Statnikov | 148/400 |
| 2007/0069720 A1* | 3/2007 | Goldfine et al. | 324/240 |
| 2007/0244659 A1* | 10/2007 | Suh et al. | 702/104 |
| 2007/0267109 A1* | 11/2007 | Kelly et al. | 148/516 |
| 2011/0163742 A1* | 7/2011 | Goldfine et al. | 324/243 |
| 2012/0013334 A1* | 1/2012 | Sheiretov et al. | 324/252 |
| 2012/0077408 A1* | 3/2012 | Tajima | 445/2 |

OTHER PUBLICATIONS

Magnetic Rubber Inspection Material. Dynamold, Inc., (source is www.Dynamold.com/margub.hmt with copyright date 2003).

* cited by examiner

COATING METHOD FOR NON-DESTRUCTIVE EXAMINATION OF ARTICLES OF MANUFACTURE

FIELD OF THE INVENTION

This invention relates generally to the field of non-destructive examination of an article of manufacture, involving stimulating an article with energy then detecting and evaluating a resulting topography of energy-induced changes in a coating on a surface of the article.

BACKGROUND OF THE INVENTION

Active thermography is a non-destructive examination (NDE) technique in which energy such as ultrasound or electromagnetic energy is applied to a test object. Discontinuities in the test object, including structural features and flaws, generate heat under such stimulation. A resulting temperature distribution on a surface of the object is detected with an infrared camera. Information about defects and the inner structure of the object can be obtained by evaluating an infrared image of the surface or a time series of such images. Each image may be digitized into picture elements, or pixels, with each pixel representing a small unit area on the surface. These digitized images can then be used for digital displays and for computer analyses in which the temperature/time series is processed and analyzed by pixel and in patterns of pixels.

Energy may be applied to a test object by electromagnetic induction, ultrasound, flash radiation, laser, hot air, or microwave excitation, for example. In a pulsed version of active thermography, the excitation power is switched on for a time period of typically 1 millisecond to over 1 second, depending on the application. The resulting energy-induced temperature distribution on a surface is temporary, constantly changing, and must be captured by a camera at each time point to be recorded. Images captured by the camera may be used to guide subsequent repairs by transposing the recorded image of a defect onto the surface of the object to guide repairs, which is a time consuming procedure and creates an opportunity for distortions or misplacement of the markings.

Another known NDE technique utilizes a vulcanizing rubber material containing specialized magnetic particles and a hardener, such as sold by Dynamos, Inc. under the product name MagRubber. The uncured rubber material is poured into a hole or other area of limited access in a ferro-magnetic part to be inspected. A magnetic field is applied to the part to cause the particles in the rubber to migrate and concentrate near regions of the article containing discontinuities, since such discontinuities concentrate the magnetic lines of flux. The rubber then cures and solidifies to form a rubber replica of the part, freezing the particles in their magnetically induced positions. The rubber replica is removed from the part, and its underside that formerly contacted the part is inspected to reveal dark lines caused by the accumulation of the particles corresponding to the discontinuities in the part.

BRIEF DESCRIPTION OF THE DRAWINGS

The invention is explained in the following description in view of the drawings that show.

DETAILED DESCRIPTION OF THE INVENTION

A new NDE process is described herein that records an energy-induced topography in a coating deposited on a surface of the test object, thus accurately and conveniently marking it for subsequent evaluation and/or repairs. This eliminates the need to transpose a recorded image of a defect onto a surface to guide repairs. The term "topography" is used herein in a broad sense to include features that have dimensional characteristics, such as a dimensional pattern formed in the coating by partial removal of the coating layer, as well as features that are non-dimensional, such as a color pattern or other varying non-dimensional characteristic.

Figure 1:
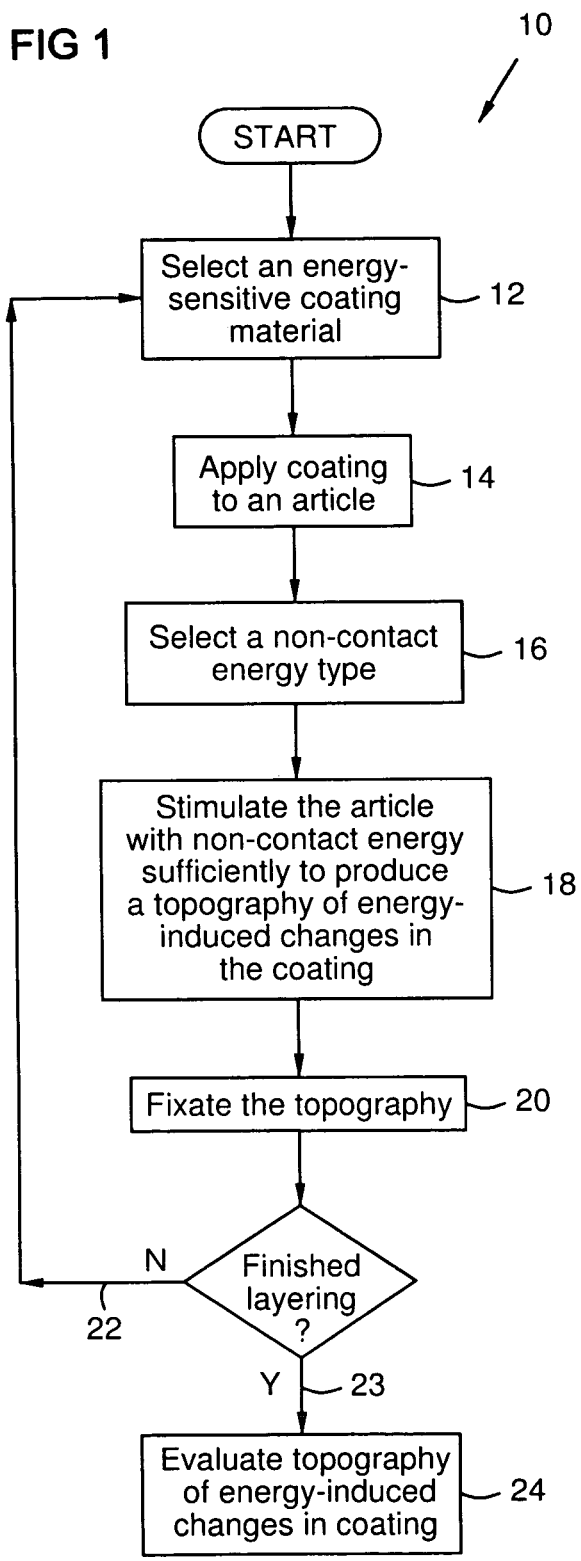
FIG. 1 is a process diagram for NDE according to one embodiment of the invention.

A method 10 for non-destructive evaluation of an article of manufacture according to one embodiment of the invention is shown in FIG. 1. An energy-sensitive coating material as later described is selected 12. This material is applied 14 as a coating to an article of manufacture to be evaluated. An energy type is selected 16 and is applied 18 to the article to produce a topography of energy-induced changes in the coating. The energy used to stimulate the article may preferentially generate heat in regions of the article proximate features such as flaws, such as in the manner of sound energy generating heat in a test article during a prior art thermography process. The resulting topography induced in the coating may then be used for evaluation of the article and to guide a repair if needed. The topography may be fixated 20 prior to such evaluation. If additional layers of energy-sensitive coatings are to be used, the method repeats 22 from step 12. When all layering or a sole layer, as desired, is complete 23, the topography is analyzed 24 to determine if features of interest in the article may be present, such as flaws, wear, separations, weakening, stress concentrations, friction damage, non-uniform material properties, fractures, heat damage, and the like.

FIGS. 2-6 illustrate partial sectional views of an article of manufacture 30 with a surface 31 and a feature, herein illustrated as a crack or discontinuity 32. Different types of coating materials 36, 38, 40, 42, 44 are illustrated in first or second coatings or layers 34, 35 in the various views.

Figure 2:
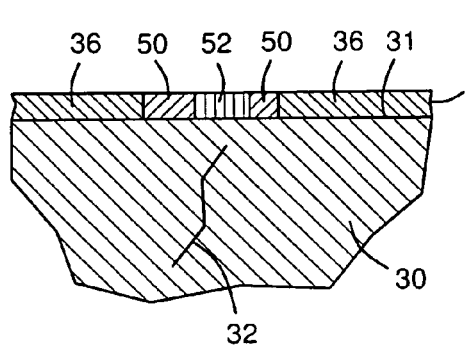
FIG. 2 is a schematic partial sectional view of an article of manufacture with an energy-sensitive coating.

In FIG. 2 a first or sole coating or layer 34 may contain a temperature-sensitive material 36, such as liquid crystals, that displays a topography of temperature-induced changes 50, 52, such as different colors responsive to localized temperature.

Figure 3:
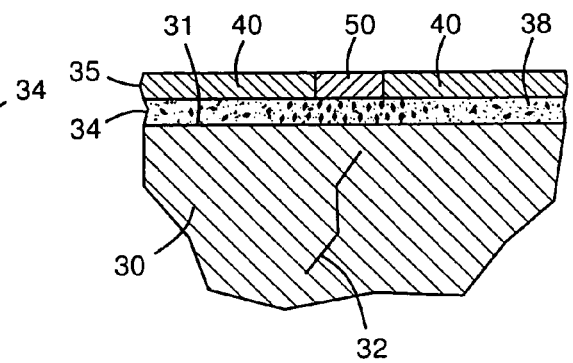
FIG. 3 is a schematic partial sectional view of an article of manufacture with two energy-sensitive coatings of different types.

FIG. 3 illustrates an article 30 coated with two layers 34 and 35, using a different type of coating material 38, 40 for each layer. Each layer 34, 35 may be selected to indicate a different aspect of discontinuities 32 in the article 30 to identify different types of discontinuities and properties such as extent and depth. The first layer 34 may be, for example, a temperature sensitive film or temperature-stimulated coating with a unique response to a relatively small temperature change indicative of subsurface or minor discontinuities. The second layer 35 may be, for example, a temperature sensitive film or temperature-stimulated coating 40 with a unique response to a higher temperature change indicative of surface or more extensive discontinuities. The film 40 may be applied as a sprayed coating or as a solid laminate with adhesive. Temperature-sensitive films are known in the field of infrared photography films. Using the method of FIG. 1, a first material 38 may be selected 12 and applied 14 to form first layer 34, then a first energy type may be selected 16 and applied 18, then the first layer 34 may be fixated 20 to freeze a topography of temperature-sensitive changes in the coating 34 relative to the discontinuity 32. A second layer 35 such as a temperature-sensitive film 40 may be selected 12 and applied 14 over the first layer 34, then a second energy type the same as or different than the first energy type is selected 16 and applied 18 to the article 30. The second layer 35 may then be fixated 20. Lastly, the energy-induced topography of both layers 34, 35 may be evaluated 24 together. In one example, if both layers exhibit a temperature-induced change in the same region, the changes may be due to a feature 32 that is relatively large or that is proximate the article surface 31. In a second example, if only the first layer 34 and not the second layer 35 exhibits a temperature-induced change in a particular region, the change may be due to a feature 32 that is relatively small or that is below the surface. In one embodiment, the layers may be clear or relatively transparent in their unchanged condition, or uppermost layer 35 may be sufficiently thin to permit visual examination of layer 34 through layer 35, in order that both layers may be optically examined together to evaluate article 30. Alternatively, the temperature-induced changes in layer 34 may be detectable through another means that does not alter the topography of temperature-induced changes in upper layer 35 so that both layers may be examined together.

The fixating step 20 may involve subjecting the coating to a fluid catalyst or fixative solution, a catalytic radiation bath, a curing temperature, or it may involve waiting for a period of time. With some coating materials a separate fixating step 20 may be unnecessary due to the inherent properties of the material, and/or the energy-induced changes in the topography may be interpreted without and/or prior to fixating.

Figure 4:
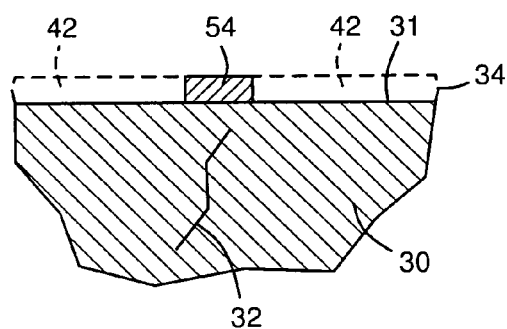
FIG. 4 is a schematic partial sectional view of an article of manufacture with a heat-accelerated curing coating such as epoxy after removal of uncured areas.

FIG. 4 illustrates an article 30 coated with a layer 34 of a heat-curing material 42 such as an epoxy resin that is mixed with a catalyst prior to the coating step 14. A heat-producing energy type such as electromagnetic induction, microwave or ultrasound may be selected that produces local temperature changes in the article 30 dependent upon the structure of the article such as the presence of discontinuities 32. During the stimulating step 18, discontinuities 32 in the article 30 generate heat, which locally accelerates curing of the epoxy 42, 54 leaving cooler areas liquid 42 and warmer areas cured 54 to a solid state after the stimulating step 18. The liquid areas 42 can then be removed with a solvent wash, leaving cured areas 54 to mark the surface 31 with a temperature-induced topography responsive to the presence of discontinuities 32 in the structure of the article 30.

Figure 5:
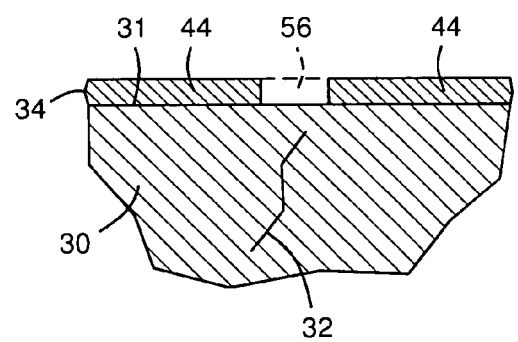
FIG. 5 is a schematic partial sectional view of an article of manufacture with a melting coating after removal of liquid areas.

FIG. 5 illustrates an article 30 coated with a layer 34 of a material 44 that melts or softens at a given temperature. A heat-producing energy type such as electromagnetic induction, microwave or ultrasound may be selected that produces local temperature changes in the article 30 dependent on structure. Prior to stimulation 18 with the selected energy type, the article 30 and coating 34 may be thermally stabilized at a temperature just below the melting point of the coating material 44. During the stimulation step 18 discontinuities 32 in the article 30 generate heat, which locally melts or softens portions 56 of the coating material 44, 56, leaving cooler areas 44 solid. The softened areas 56 can then be removed with a solvent wash, leaving solid areas 44 to mark the surface 31 with a temperature-induced topography that indicates discontinuities 32 in the structure of the article 30.

Figure 6:
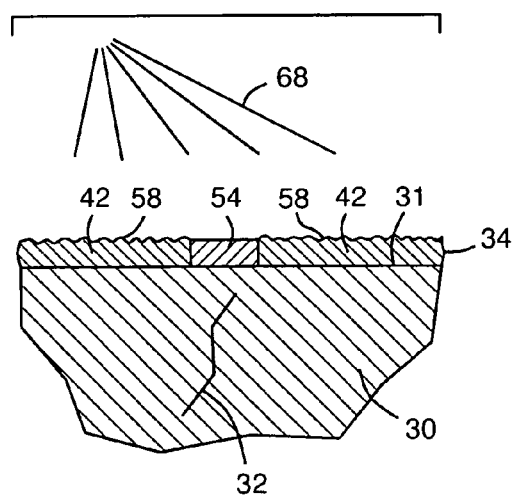
FIG. 6 is a schematic partial sectional view of an article of manufacture with a heat-accelerated curing coating after stimulation then spraying with a soft surface modifying spray.

As shown in FIG. 6, instead of washing a heat-curing coating 34 as in FIG. 4 to remove unchanged areas 42, the coating 34 may be sprayed 68 with a gas, liquid, or powder that affects the uncured areas 42 preferentially over the cured areas 54. Such spraying 68 may create a change 58 such as a surface texture, a deposition or removal of material, or a chemical reaction in or on the uncured areas 42, resulting in a change in reflectivity or other properties of the uncured areas 42. Such changes 58 can then be fixated 20 by heating the coating 34 to cure it over the whole surface 31. A similar process may be used wherein the spray 68 creates a change in the cured area 54 but not in the uncured area 42, and that change is then fixated.

Figure 7:
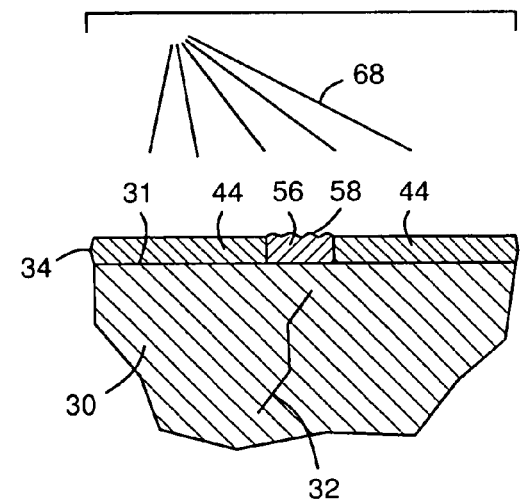
FIG. 7 is a schematic partial sectional view of an article of manufacture with a melting coating after stimulation then spraying with a soft surface modifying spray.

As shown in FIG. 7, spraying 68 may also be used with a melting or softening coating material 44 instead of washing as in FIG. 5. Spraying 68 may produce changes 58 in softened areas 56 of the coating 34 preferentially over unsoftened areas 44. These changes may then be fixated 20 by allowing the softened areas 56 to cool below the softening temperature.

An energy-sensitive coating material may be selected 12 from among the types described above and others that respond to a localized energy change with a respective localized change in color or texture or crystal structure or phase of matter or a magnetic property or conductivity or capacitance or impedance or volume or surface tension or phase alignment or polymer chemistry or curing or adhesion or reflectivity or other detectable parameter. A temperature-sensitive coating material may be selected for sensitivity to temperature changes of less than 3° C. in one embodiment.

Figure 8:
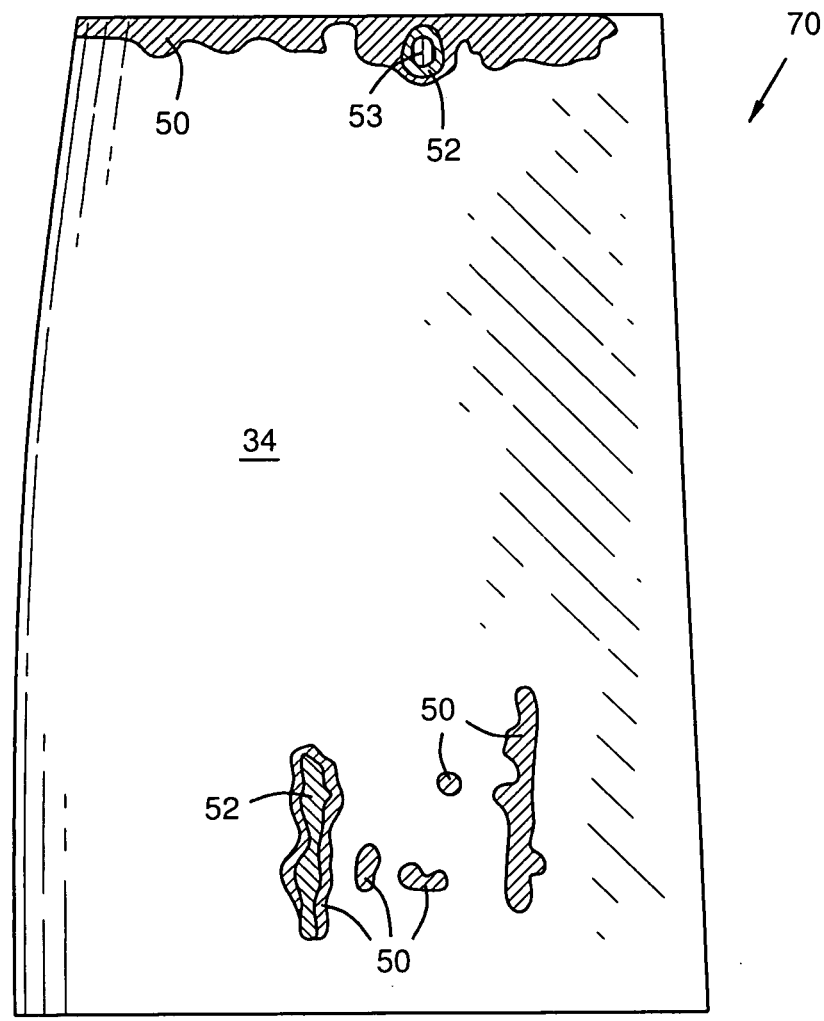
FIG. 8 is a side view of a turbine blade with a topography of energy-induced changes marked thereon by at least one energy-sensitive coating.

FIG. 8 illustrates a turbine blade 70 with an energy-sensitive coating 34 displaying a topography of heat-induced changes 50, 52, 53 after stimulation of the blade 70 with sonic energy. Such topography may be fixated and the blade then subjected to further processing, such as evaluation of the topography and/or repair operations.

Figure 9:
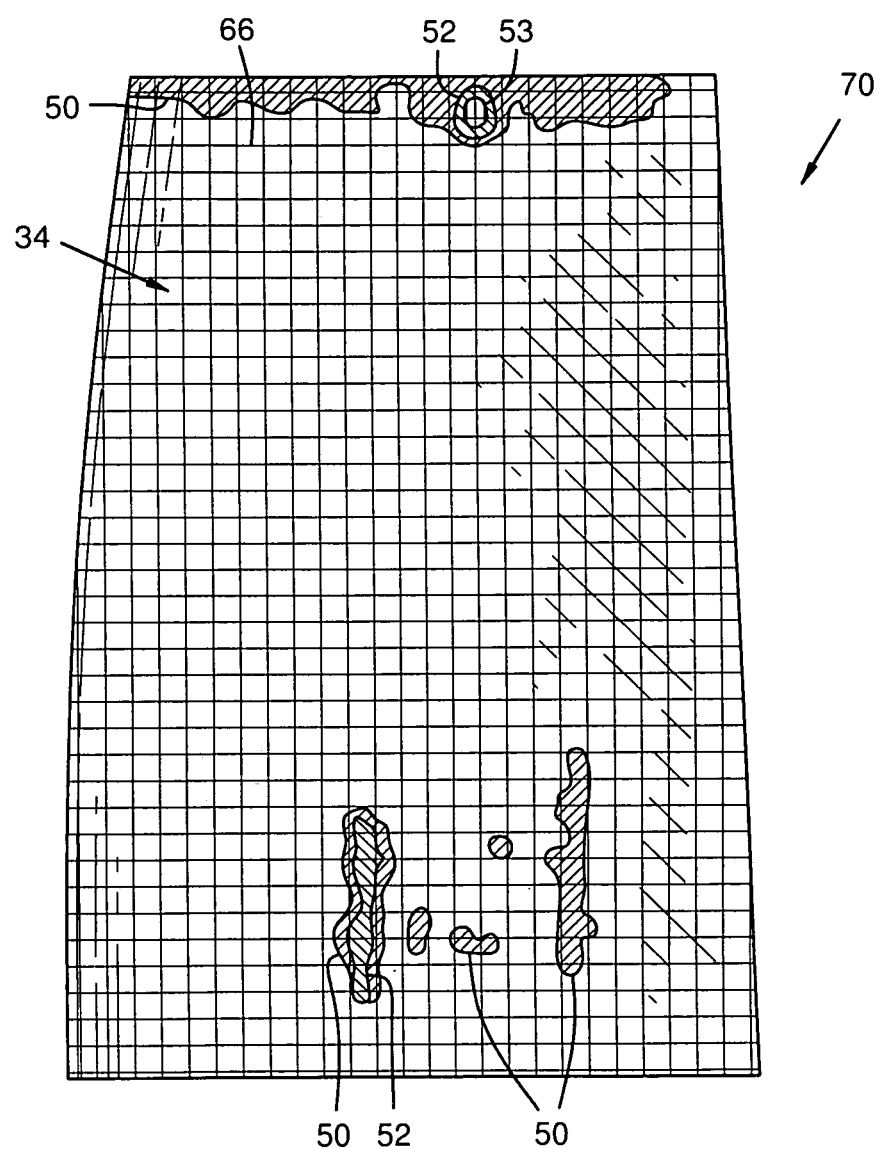
FIG. 9 is a side view of a turbine blade with a topography of energy-induced changes and a repeating pattern marked thereon by at least one energy-sensitive coating.

As illustrated in FIG. 9 with a turbine blade 70, an energy-sensitive coating 34 may be applied in a repeating pattern 66 such as a grid of known scale, or the coating 34 may be overlaid with such a pattern 66 in a second layer. The analyzing step 24 may then evaluate the topography of energy-induced changes 50, 52, 53 in conjunction with the repeating pattern 66 to determine dimensions of discontinuities 32 in the article. Further, the repeating pattern 66 may be applied at a known position relative to the surface 31, or the repeating pattern 66 may include one or more missing or different segment of known registration, so that the analyzing step 24 may determine both location and dimensions of each discontinuity 32. To produce a repeating pattern 66, an energy-sensitive layer 34 may be applied with lines of omission between areas of coating material, the lines of omission defining the repeating pattern 66. Alternately the pattern 66 may be produced by first applying an energy-sensitive layer 34, stimulating it 18, and fixating it 20, then overlaying it with a second layer defining lines 66. The layer of lines 66 need not be energy-sensitive. It may serve only to register a position and scale of the topography 50, 52, 53 displayed by the first layer 34.

The coating step 14 may be performed by known methods such as dipping, spraying, laminating, and the like. Energy may be applied to the article in any known manner effective to produce a change in the coating selectively in regions associated with a feature of interest in the article, such as a discontinuity, crack, edge, porosity, etc. Generally, the energy applied to the article may be transformed by the feature of interest into a form of energy effective to cause the change in the coating. In this way, the energy applied to the article does not produce a general change in the coating, but rather, produces the change only in regions associated with features of interest. Thermography is one example of such a process wherein mechanical energy (sound) is imparted into the article and causes friction between surfaces of a feature such as a crack to produce heat energy local to the feature. The heat energy then produces a change in the coating applied to the article. After evaluation and repair, if needed, washing, blasting or the like may be used to remove any remaining coating material. Depending on the selected coating material and energy type, some methods for detecting energy-induced changes in the coating may include as follows:

1. Changes in optical properties such as color, light transmission, and reflection may be illuminated for detection by human eye or camera with visible light, fluorescent light, monochromatic light to eliminate an unwanted background or to enhance a desired effect, or polarized light to eliminate secondary reflections.

2. Changes in electromagnetic properties such as electrical conductivity, capacitance, impedance, and magnetic alignment may be detected by Hall Effect sensors, eddy current methods, microwave methods, dielectrometers, induction methods, and charge detectors as known in the art of NDE.

3. Changes in texture or crystalline structure may be revealed with illuminating radiation such as structured light patterns, polarized light, ultraviolet radiation, infrared radiation, or x-rays, and may then be detected by human eye or appropriate camera, or by physical measurement such as with a stylus.

4. Changes in phase, volume, or phase alignment may be detected directly with metallographic methods or by known indirect methods if the change results in an externally measurable property such as velocity, permeability, elasticity or plasticity.

5. Changes in surface tension, polymer chemistry, local curing, and local adhesion all affect removability of areas of the coating. Controlled washing/cleaning may be used to remove affected or unaffected portions of the coating, leaving other portions as described previously.

In a further embodiment, the coating that is selected 12 may be both temperature sensitive and photosensitive, for example including both liquid crystals and photosensitive chemicals such as silver halides. In this embodiment, the coating would be applied 14 to the test article in a dark environment (dark in the sense of lacking wavelengths of electromagnetic energy to which the chemicals are sensitive). The article would then be exposed to electromagnetic energy in conjunction with being stimulated with energy 18 to develop a feature-responsive image in the coating resulting from the response of the liquid crystals to the selective temperature rise in regions of the article proximate features. The photosensitive chemicals would then be fixed to arrest the photo development, thereby preserving a "picture" of the topography within the coating. In this manner, otherwise invisible features in the article can be made detectable by the unaided human eye or otherwise in the form of a feature-responsive coating that remains affixed to the article. The photosensitive chemicals may include silver halides for producing a simple black and white image in the coating or they may include other chemicals to provide sensitivity to selected wavelengths of electromagnetic energy (e.g. visible light colors, infrared, ultraviolet, etc.). Such wavelength selectivity may be useful when the coating displays different reflectivity (colors) in response to different temperatures, thereby enabling a further degree of evaluation of the underlying features.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A method for non-destructive evaluation of an article of manufacture, the method comprising the following sequence of steps:

coating a surface of the article with a temperature-sensitive coating;

stimulating the article with an evaluation energy that preferentially generates heat in the article proximate a flaw therein, producing temperature-induced changes in the temperature-sensitive coating that visibly indicate the flaw in the article, wherein the evaluation energy is selected and controlled for evaluation of the article;

evaluating the article via the temperature-induced changes in the temperature sensitive coating;

conducting a repair on the article using the temperature-induced changes in the temperature-sensitive coating on the surface of the article as a guide for locating the repair; wherein:

the coating step comprises applying the temperature-sensitive coating in a grid pattern at a particular scale on the surface; and the evaluating step comprises evaluating the temperature-induced changes in conjunction with the grid pattern to determine a dimension of the flaw in the article.

2. A method for non-destructive evaluation of an article of manufacture, the method comprising the following sequence of steps:

coating a surface of the article with a temperature-sensitive coating;

stimulating the article with an evaluation energy that preferentially generates heat in the article proximate a flaw therein, producing temperature-induced changes in the temperature-sensitive coating that visibly indicate the flaw in the article, wherein the evaluation energy is selected and controlled for evaluation of the article;

evaluating the article via the temperature-induced changes in the temperature sensitive coating;

conducting a repair on the article using the temperature-induced changes in the temperature-sensitive coating on the surface of the article as a guide for locating the repair; wherein:

the coating step comprises applying the temperature-sensitive coating in a grid pattern at a particular scale on the surface;

the evaluating step comprises evaluating the temperature-induced changes in conjunction with the grid pattern to determine a dimension of the flaw in the article;

the coating step further comprises applying the grid pattern at a particular position on the surface; and the evaluating step further comprises evaluating the temperature-induced changes in conjunction with both the position and the scale of the grid pattern to determine a location and the dimension of the flaw.

3. The method of claim 1 wherein the article is a turbine blade.

4. The method of claim 2 wherein the article is a turbine blade.

* * * * *